United States Patent [19]

Lindenmeier et al.

[11] Patent Number: 5,749,869
[45] Date of Patent: May 12, 1998

[54] HIGH-FREQUENCY SURGICAL GENERATOR FOR CUTTING TISSUE

[75] Inventors: Heinz Lindenmeier, Planegg; Georg Lohr, Ottobrunn; Karl Fastenmeier, Munich; Gerhard Flachenecker, deceased, late of Ottobrunn, all of Germany, by Hildegard Flachenecker, legal representative

[73] Assignee: Karl Storz GmbH & Co., Tuttlingen, Germany

[21] Appl. No.: 457,106

[22] Filed: Jun. 1, 1995

Related U.S. Application Data

[62] Division of Ser. No. 193,109, Jul. 18, 1994.

[30] Foreign Application Priority Data

| Aug. 12, 1991 | [DE] | Germany | 41 26 607.2 |
| Oct. 24, 1991 | [DE] | Germany | 41 35 180.2 |
| Oct. 24, 1991 | [DE] | Germany | 41 35 184.3 |

[51] Int. Cl.⁶ ............................................. A61B 17/39
[52] U.S. Cl. .................................. 606/34; 606/32; 606/39
[58] Field of Search ....................... 606/32–34, 37–42

[56] References Cited

U.S. PATENT DOCUMENTS

| 5,108,391 | 4/1992 | Flachenecker et al. | 606/38 |
| 5,133,711 | 7/1992 | Hagen | 606/38 |
| 5,267,997 | 12/1993 | Farin et al. | 606/38 |
| 5,300,068 | 4/1994 | Rosar et al. | 606/34 |
| 5,364,392 | 11/1994 | Warner et al. | 606/34 |
| 5,472,443 | 12/1995 | Cordis et al. | 606/48 |

*Primary Examiner*—Jennifer Bahr
*Assistant Examiner*—Michael Peffley
*Attorney, Agent, or Firm*—Donald D. Mon

[57] ABSTRACT

The present invention relates to high-frequency generator for cutting tissue having adjustment devices, with which at least one of the momentary electric output values, such as e.g., current, voltage, power or electric arc can be set.

The present invention is distinguished by, for improvement of the initial incision behavior, an electronic desired-value transmitter and a measurement device having an evaluation unit for direct and/or indirect determination of cutting being provided and said electronic desired-value transmitter providing upon commencement of an incision a particularly suited generator setting for the initial incision as long as said measurement device signals tissue-separating cutting of the probe and thereupon providing a lower desired value for the generator in such a manner that normal cutting corresponding to the desired surgical goal ensues.

6 Claims, 7 Drawing Sheets

HIGH-FREQUENCY SURGICAL GENERATOR FOR CUTTING TISSUE

CROSS REFERENCE TO OTHER PARENT APPLICATION

This is a division of applicant's presently co-pending U.S. patent application Ser. No. 08/193,109 filed Jul. 18, 1994, entitled "HIGH FREQUENCY SURGICAL GENERATOR FOR CUTTING TISSUE".

TECHNICAL FIELD

The present invention relates to a high-frequency generator for high-frequency surgery according to the generic parts of the alternative embodiments disclosed.

STATE OF THE ART

High-frequency currents are employed in surgery for cutting biological tissue or for coagulating, i.e. to stop bleeding.

High-frequency currents are used in surgery, in particular, for the removal of tissue if the operation site can be reached through natural body openings, however a scalpel can not be used without opening the patient's body. For example, in urology, tumors in the bladder or excrescences of the prostate gland can be removed with the aid of high-frequency currents using transurethally entered surgical instruments. In a similar manner, in enterology, e.g., polyps can be removed from the intestine walls. The cutting electrode of the surgical instrument only cuts as long as the generator delivering the high-frequency current is activated, thus ensuring, in this way, safe entry and removal of surgical instruments through the natural openings of the patient's body.

In some conventional generators at least one electric output value, such as current, output voltage, power, no-load voltage or internal resistance can be set. This setting can directly or indirectly influence the output power. This output power has to be set according to the purpose of the surgery and the conditions at the site of the operation.

One problem in high-frequency surgery is the correct dosage of the momentarily applied high-frequency power. The minimum required high-frequency power for good cutting can fluctuate strongly. It depends on the consistency of the tissue, the conductivity and the water content of the tissue, the shape and size of the electrodes, the cutting depth and speed, and other electric parameters subject to certain, in many cases, very abruptly occurring changes in the course of an operation. The usual high-frequency setting arrived at through experience, therefore, results in, on the average, clearly too great a high-frequency power to the risks of which the surgeon has to consciously expose his patient and himself. In order to be able to keep these risks to a minimum, respectively to be able to almost exclude them, the momentary output power of the high-frequency generator would have to be controlled automatically in such a manner that it corresponds at all times to the minimum absolutely necessary.

A particular problem is the commencement of cutting. Depending on the state of the probe and of the tissue, the start conditions can vary greatly. The probe can be blank metal with a clean surface and therefore highly conductive. It can, however, after several incisions or coagulations just as well be covered with an insulating layer of oxide or of carbonized tissue residue. A high generator voltage is required in order to penetrate this layer. Decisive for the penetration of this insulating layer is the electric field strength which has to be above the disruptive field strength of this layer. The generator has to deliver a correspondingly high voltage.

The tissue itself can be changed by the preceding incisions or coagulations. Particulary difficult is the initial incision in surgery in the stomach or intestines. The tissue surface is very moist here and especially highly electrically conductive. In this case, too, the initial incision can only be carried out with a very high generator output. Important is a high power input and thus a high generator current in order to vaporize the conductive fluid as quickly as possible.

If the power supply from the generator is constant, the surgeon has to set the generator in such a manner that it delivers the required power for the initial incision. As laboratory and clinical measurements reveal, this power required for the initial incision is substantially above the power required for the continuation of cutting. The surgeon will continue cutting with an unaltered setting and thereby chance the known risks involved with an excessive power output.

If the initial incision is not possible with a specific generator setting, the energy input will result in coagulation of the surface of the tissue, which as a result becomes even more high-ohmic and an initial incision is now hardly possible at this site. At least a substantially higher generator power output generator is necessary therefor.

A solution to this problem is described in the German patent P 25 04 280. In this apparatus, the size of the electric arc between the cutting electrode and the tissue to be cut is determined with the aid of an indicator unit and the electric signal derived therefrom is transmitted to an adjustment device. This adjustment device compares this signal with the desired-value program of a desired-value transmitter and derives therefrom a variable which sets the amount of the generator output current in such a manner that the intensity of the electric arc follows the desired-value program. With this adjustment, the minimum required output for cutting is set at any moment. However, the technical complexity involved in the realization is considerable. Another solution is, therefore, necessary in order to obtain a simple and economical high-frequency surgical generator.

Another suggested solution is the proposed device in the German published application DE 3420340. It raises the output for a constant, preset time following switching on the generator. As laboratory and clinical measurements show, the energy required for the initial incision fluctuates considerably. An increased power output over a preset time rarely meets the demands arising in practice. Moreover, when applying this process it is absolutely essential that the probe is in contact with the tissue when the generator is switched on, because the raised power output is delivered immediately after the generator has been switched on. If there is no contact with tissue until a short time after switching on the generator, the generator will be delivering its normal cutting power and the device will no longer be effective.

Other problems, but also special possibilities are yielded by high-frequency surgery if there is not only homogeneous tissue at the site of the operation or other types of materials are present at the operation site.

Thus, e.g. in the case of prostatectomy, the adenoma tissue which is to be resected differs from the tissue of the prostata capsule which must not be severed. Another example is cutting in the vicinity of large blood vessels. Here an incision can often entail hemorrhaging that is difficult to contain. If a blood vessel can be identified, the generator output can be reduced so low that cutting is no longer possible. The vessel can be closed by subsequent coagulation.

If the cutting electrode comes into contact with bone during an incision, the bone can be thermally damaged. This danger is particulary great in dentistry. Here it is easy to penetrate too deeply into the thin gum layer and to come into contact with the jawbone. For this reason, they too should be identified by the generator.

Particulary lasting negative effects of high-frequency surgery occur if the cutting electrode comes into contact with metallic conductive elements in the patient's body such as implants, screws, nails, fillings in teeth, crowns or even surgical instruments such as tweezers, mirrors or shafts of resection instruments. In this case, the high-frequency current runs off the cutting electrode spreading over these metallic elements to the surrounding tissue. At the points of transfer large-surface coagulation can occur. The European patent 91100442.2 describes an apparatus which restricts the generator output current. With it, tissue damage occurring when the cutting electrode comes into contact with metallic conductive elements can sometimes be reduced. The power delivered to the tissue in response to the current limit at the operation site is proportional to the real part of the impedance from the transfer of the metallic conductive element to the surrounding tissue. In this way the effectivity of this device is inversely proportional to the impedance of the tissue transition. In the case of small-surface tissue transistions, the impedance is very high and therefore also the stray power. These small-surface tissue transitions, in particular, may only be exposed to little power. Thus, the most sensitive tissue sites, in particular, are least protected by this protective device. This process is also only suited for special applications, because the tissue impedance in the case of normal incisions without contacting metal can fluctuate by more than one magnitude. This is the result of the great fluctuation range of cutting parameters such as the cross-section of the electrode, cutting depth of the electrode, cutting velocity and the electric arc always burning between the cutting electrode and the tissue during cutting. Therefore, with this process, there is a very great danger that there is not enough current available for a rapid incision, thus handicapping the surgeon. On the other hand, there is also the danger that metallic conductive elements only come into contact with the tissue in small-surface areas. In this case, the transferred power is high despite the current limit, and as a consequence bad burns may occur. The process fails totally if, in the vicinity of the tissue to be cut, there is high-ohmic tissue which must not be cut or which must not be exposed thermally.

Another problem in high-frequency surgery is the interference of other devices and apparatuses as well as the stimulation of the patient's nerves and muscles.

Various devices are influenced by the high high-frequency power utilized in high-frequency surgery. Interference, therefore, may couple in inductively, capacitatively or through radiation. Often the high-frequency surgical generator does not transmit a narrow-band signal with the basic generator frequency but rather a wide spectrum in the range of several Hz to several MHz due to leading edges and modulation. Even with generators that primarily transmit power only on the ground wave, harmonics of the generator frequency are generated by the occurrence of electric arcs on the probe due to their non-linearities. In this way, devices are frequently influenced and disturbed if they are not designed especially immune to interference. The interference difficulties, however, can generally be decreased by upgrading the devices in question. Another possibility of minimizing, particularly, the effects of interference in videocamera pictures is described in the European patent 0429204A1. In it the pulsed output signal of a high-frequency surgical generator is synchronized with the signal from a video camera in such a manner that the high-frequency interference caused by the generator only influences non-vital parts of the picture of the camera. Blanking-out with such a high frequency results in a high-frequency signal having a high crest factor as is usually utilized for coagulation. Due to the coagulation generated thereby, low necrotic cutting is not possible. Cutting without disturbing necrosis is not possible until blanking-out is performed with frequencies below 1000 Hz.

A much more crucial influence are the effects on the patient's body. Although high-frequency surgery is based on the thermal effect of current, the electrical effects are not negligible. With signals having generator frequencies of 300 kHz (in compliance with VDE regulations) usual today, there is no detectable stimulation of the muscles or nerves. However, due to the electric arcs always occurring during cutting, there is a fraction having very low frequencies close to 0, the 0th harmonic of the generator signal. Due to this fraction which, as measurements show, can actually occur with amplitudes up to several volts, stimulation of muscles and nerves is possible. These, however, are undesirable and often dangerous. Energy of 10J already suffices to trigger muscle contraction. This may lead to sudden, major movements by the patient on the operating table. As a consequence, the patient may be injured. Substantially more dangerous is, however, stimulation of the heart muscle. Therefore, even short pulses having an energy of 400 Ws can lead to heart chamber fibrillations. In this self-induced state the heart muscle beats so fast that the amount of blood pumped through may be very small, and the body is insufficiently supplied with blood. The result is death. In hospitals, heart chamber fibrillations can be eliminated with defillibrators. In many applications of high-frequency surgery, such as in small practices of physicians or dentists such a device is not available.

There are numerous ways of avoiding these dangerous side effects. The simplest one is avoiding potentially risky surgery, such as in the vicinity of the heart. Also high-frequency surgery techniques are often ruled altogether with potential-risk patients, such as bearers of pacemakers. Another possibility is reducing the danger, if not eliminate it, is minimizing the power utilized for high-frequency surgery. In this way, the dangerous low-frequency currents are also at a minimum. This is, e.g., possible with the apparatus described in the German patent 2504280. It measures the intensity of the electric arc and transmits to the patient only the minimum energy required for maintaining the electric arc needed for cutting.

High-frequency surgery offers such substantial advantages in many surgical techniques that its use should also be possible in potentially risky areas of the bodies of potential-risk patients. Thus, especially gentle endoscopic surgery is important in older patients who, however, often have a pacemaker.

DESCRIPTION OF THE INVENTION

The object of the present invention is, therefore, to improve a high-frequency generator for high-frequency surgery in such a manner that undesirable side effects of any kind are excluded or at least permanently reduced.

This relates, in particular, to adapting to the conditions at the surgical area in such a manner that rapid and almost coagulation-free incision is achieved. Furthermore, the invented high-frequency generator should detect differing materials, especially also metallic, conductive elements, and differing types of tissue in the vicinity of the cutting electrode so that the power from the generator can be adapted to the desired surgical purpose.

Another requirement of the design of the high-frequency generator is to minimize the interference of other devices, respectively, the potentially dangerous stimulation of certain muscles and nerves.

This object is solved in accordance with the present invention with the measures disclosed in the alternative embodiments.

With the aid of a measurement device for direct and/or indirect determination of the cutting, the high-frequency generator having adjustment device for setting the momentary electric output value is provided by a desired-value transmitter. Immediately upon activating the generator, the desired-value transmitter provides a desired value for a generator setting, which is especially suited for the initial incision. This may be, depending on the impedance conditions at the operation site, raised generator voltage, raised generator current or also raised generator power. In accordance with the adjustment characteristics of the generator, the desired value can also be provided for another electric value corresponding to the power, such as voltage or current. A measurement device determines the commencement of cutting by the probe. The probe cuts as soon as it penetrates the tissue separating the cell systems. Usually an electric arc occurs simultaneously between the probe and the tissue. As soon as cutting is determined, the desired-value transmitter provides a lower desired value for the generator so that an incision can be made without undesired tissue coagulation. In this way, the average power input during an incision is substantially lower than with a constant generator setting to a value at which an initial incision is possible.

An especially advantageous embodiment consists of the measurement device for direct and/or indirect determination of cutting detects probe movement in the tissue. This may be, e.g. followed by distance measurement. If the probe enters deeper into the tissue than the distance prescribed by a desired-value transmitter, cutting is signalled.

A certain characteristic sign of high-frequency surgical cutting is the electric arc that occurs between the probe and the tissue. Thus, a further advantageous embodiment is that the measurement device (2) for direct and/or indirect determination of cutting detects the electric arc occurring on the probe. This can, preferably, ensue by spectral observation of the generator output signal. For this purpose, a high-frequency generator for high-frequency surgery having an apparatus for setting the maximum output power is controlled by the output signal of an indicator device and an evaluation circuit. The electric power contained in at least two frequency ranges is used for control. The output signal from an auxilliary oscillator can selectively be superimposed over the power oscillation signal. Now the mixed products resulting from the electric arc can be evaluated and detected.

A detailed description of this solution variant ensues in conjunction with the specific design of the high-frequency generator in order to detect differing materials.

A further characteristic sign of the commencement of cutting is, as measurements have shown, the rise in impedance between the probe and the tissue. This jump in impedance is especially marked when cutting tissue in the stomach and intestines. Here the highly conductive fluid and mucous layer on the surface must be vaporized before it is possible to cut in the tissue layers lying underneath. For this reason, a further advantageous embodiment is that the measurement device for direct and/or indirect determination of the cutting evaluates the impedance between the probe and the neutral electrode. In this case, too, the output signal from the high-frequency generator or the output signal of an auxilliary generator can be employed selectively.

Dependent on the state of the tissue, different generator settings are necessary for rapid initial incision. An advantageous embodiment, therefore, is that a desired-value transmitter is provided which Gives a high generator current in the event that at the commencement of cutting the tissue impedance at the probe is low-ohmic. Another advantageous embodiment is that a desired-value transmitter is provided which gives a high generator current in the event that at the commencement of cutting the tissue impedance is high-ohmic.

By timely detection of differing materials, in particular, metallic elements in the vicinity of the cutting electrode, the power can be lowered to a safe value at which cutting is no longer possible and at which there is no danger of coagulation. The surgeon can also be warned selectively or in addition.

For this purpose the high-frequency generator has, in accordance with the present invention, an indicator device which compares the spectrum of the power at the output of the generator influenced by the electric arc or a value dependent on it such as current or voltage in at least two different frequency ranges. A desired value that influences the generator power is transmitted according to the results of this comparison. Differences in electro-physical properties are utilized to characterize the varying materials. These properties influence the electric arc which occurs between the cutting electrode and the tissue upon cutting in high-frequency surgery. This electric arc bridges the vapor layer between the electrode and the tissue, this vapor layer resulting from the vaporization of the cell fluid. This electric arc does not burn evenly over the entire surface of the cutting electrode. The electric arc, on the condition that the voltage is sufficiently high, ignites where the vapor layer is the thinnest. The great concentration of energy generated by the electric arc ensures rapid vaporization of the cells at the arcing over points. A stronger layer of vapor forms here and the electric arc moves to another point where the insulation is less thick.

Characteristic for a typical cutting procedure are the difference in material of the cutting tool and the cutting object. The principle of a case of tissue being cut with a metal electrode frequently arising in practice is described, by way of illustration, in the following. Metal and tissue passes different physical properties, such as electron affinity. This effect is intensified by the difference in temperature of the materials. Thus, due to the vaporization of the cell fluid contained in it, the tissue will not at first assume temperatures above the boiling point of this fluid. Consequently, the ignition and burning voltage of the electric arc differ depending on whether the metal momentarily has more negative potential or the tissue. If the metal is the cathode, the ignition voltage is lower than in the tissue. Thus, when a high-frequency alternating voltage is applied, current flow sets in at different times depending on polarity. This asymmetry can be measured by spectral evaluation. Depending on the combination of cutting electrode and cutting object, a characteristic spectral distribution of power sets in.

If there is a body of a different material so close to the cutting electrode that the electric arc jumps over at it, the symmetry of the current flow changes due to the different electric properties of the materials and, therefore, also the spectral distribution of power in the output signal of the generator. The different spectral distribution of power can be evaluated by comparing at least two not identical frequency ranges.

The evaluation of the spectral distribution of power permits differenciating between different materials. A typical example is differing between tissue and metallic conductive bodies. With a more detailed evaluation, it is possible to even differentiate between several types of tissue. Identifying the material permits adapting the generator power to the conditions at the operation site. Thus, the generator can be switched off directly prior to contact with metallic conductive materials in order to avoid coagulating the surrounding tissue. Differenciating between tissues permits, e.g., removing only the adenoma tissue in prostate resection. Cutting into the capsule, which would result in perforation, can be prevented.

An especially advantageous embodiment is described in the following. If materials have similar electric properties, predominantly odd harmonics of the generator frequency occur due to the electric arc, whereas if the materials have different electric properties, only even harmonics of the generator frequency occur. If the materials are the same, only odd harmonics of the generator frequency occur. The term "harmonics" refers to the multiples of the generator frequency including the harmonics of the 0th order, which corresponds to the direct current part of the frequency (f=o). Therefore, a particulary advantageous embodiment has two filters for evaluating the spectral fractions of the generator signal provided in the indicator device, the first filter determining predominantly the spectral performance with one or several odd harmonics of the basic frequency of the generator $f_O$ and the second filter predominantly determining the spectral performance with one or several even harmonics oh the basic frequency of the generator $f_O$. This embodiment is especially suited for use in detecting metallic bodies in the tissue.

In order to detect differing materials, an auxilliary oscillator signal of lower power having the frequency $f_H$ is additively superimposed on the generator signal having the frequency $f_O$. Therefore, distortions result from the non-linearity of the electric arc, and thus mixed products of a higher order. With similar materials, mixed products of the second order having the frequencies $2 f_O$, $2 f_H$, $f_O+f_H$, $f_O-f_H$ result, whereas mixed products of the third order having the frequencies $3 f_O$, $3 f_H$, $2 f_O+f_H$, $f_O+2 f_H$, $2 f_O-f_H$, $f_O-2f_H$, $f_H+f_O-f_O$ result with differing materials.

For this reason, another advantageous embodiment has an auxilliary oscillator signal superimposed on the generator signal. The evaluation is determined by the first filter of one or several mixed products of a second order and by the second filter of one or several mixed products of a third order. Processes of this type are especially advantageous if the generator is not sufficiently free of harmonic waves or if the generator frequency is not stable enough so that filtering out the harmonics would be very complex.

A particularly advantageous embodiment for utilizing the gained information on the difference in tissue or other materials is to employ this data for the adjustment of the generator power or for a major reduction of the generator power in such a manner that no incision and/or coagulation is possible in the tissue.

Another embodiment is a warning device Which warns the user of the high-frequency surgical generator. The user can then identify conditions and, e.g. select a different manner of conducting the cutting, switch off the generator, or replace faulty surgical instruments.

A reduction of the generator power is advantageously controlled via a time element in such a manner that following the identification of a certain tissue or other material, the generator power remains lowered for a specific time. In this way, it is avoided that unnecessarily high power is delivered to the tissue by raising the generator power too frequently, because after lowering the generator power no electric arc can occur and the indicator device is no longer able to determine the material or the tissue. Without a time element, the power would rise again immediately following the drop in power. The time of the time element may last a halfwave, but it may also last substantially longer. For special applications, it may be useful not to permit activation of the generator until there is a new incision.

In addition, a monitoring of the tissue impedance can be built in. It detects jumps in impedance, such as, e.g., those occurring during removal of the cutting electrode and then terminates the time interval of the timer.

A high-frequency generator for the high-frequency surgery which can be regulated by its output power or by one of the electric values dependent thereon in order to minimize the interference of other devices, respectively the stimulation of certain muscles and nerves has a blanking-out device with the aid of which the output power of the generator can be reduced. Depending on the application, the generator can have no, one or several adjustments of its output values. The blanking-out device is, in accordance with the present invention, controlled by a measurement device for determination of the protection times. For this purpose, the output power of the generator is completely turned off or reduced in such a manner that interferences caused directly or indirectly by the generator signal may be ignored. Among these interferences are also disturbances occurring due to modulation and/or non-linear effects outside the generator. A particularly time-dependent non-linearity is the electric arc. In this manner, no interferences from other electronic devices or muscle and nerve stimulation can occur during the protected times. The time intervals in which the generator power is reduced can be longer than or also temporally staggered in relation to the time intervals determined by the measurement device for determination of protected times. This may be, e.g., necessary in order to permit discharging the series capacitor provided at the generator exit in compliance with VDE safety regulations. This series capacitor may be charged during the cutting by the direct current part of the voltage generated by the non-linearity of the electric arc. At the beginning of the protected time interval, the charge must have been discharged from the capacitor in time, because otherwise the discharging current may cause stimulation of the muscles and nerves. The time intervals should be selected so large that the original surgical purpose does not change. In this manner, the modulation of a generator signal primarily designed for cutting cannot result in a predominantly coagulating function. Furthermore, the generator has a device for fixing the internal conditions according to the time intervals in which the generator power is reduced. In this way, desired values and settings for the following time interval can be provided for the internal circuit components of the generator and its control and adjustment device. These desired values and settings can be fixed or variable and permit adapation to the surgical goal.

Characteristic for control units, like those utilized in high-frequency surgery generators, is their time constant which is substantially larger than the duration of the generator frequency period has to be. In the case of an incision with periodic interruptions, this control unit would have to respond at the beginning of each cutting interval. This can lead to coagulation. The cutting quality, therefore, deteriorates. Characteristic for an incision with such short interruptions is, however, that the physical properties of the tissue at the operation site only change insignificantly. Thus, it would be possible to continue cutting with the same parameters of the generator setting. In order to do this, not only the provided values for the parameter settings are stored, but the internal conditions of the control unit is also retained.

An especially advantageous embodiment is that the generator is provided with a memory unit for storing all the important parameters, in particular the conditions of the internal control unit. An example would be realization with analog memories in the case of analog control unit and, in the case of digital control unit, realization with digital memories. Storage of the values always occurs at the end of the cutting interval at the beginning of the pause. At the beginning of the next time interval at the end of the pause, these values are requested and utilized to initialize the control unit. In this manner, a quick response of the control unit and therefore rapid and tissue-gentle cutting is attained.

Another advantageous embodiment is that a desired-value transmitter is provided which provides desired values for the adjustment of the output power after the interval in which the generator power is reduced. These desired values can correspond to average generator powers in average operations. In this way, a defined initial incision behavior of the generator is obtained at the end of the protected interval, because the control unit does not proceed from a zero condition, but rather a starting condition very close to actual cutting conditions.

In the case of extended protected intervals, the conditions at the operation site may change gradually. Therefore, a further advantageous embodiment is that a desired value for greater power can be given selectively also when resuming cutting. In this way, the energy required for to start cutting could be delivered to the tissue in the shortest time. As soon as the measurement device for determination of cutting detects the commencement of cutting, the power is switched down to lower, just barely sufficient power for cutting. In this manner, the effects of cooling or a collection of fluid in the tissue is compensated and a rapid initial incision is obtained with only little coagulation.

Another advantageous embodiment is that the measurement device for the determination of protected times determines the protected intervals based on the patient's heart rhythm, which can be derived from, e.g., electrocardiogram signals. Particularly in the case of operations in the vicinity of the heart or in the case of pacemaker bearers, the power output of the generator could be restricted to those times, in which the heart muscle cannot be stimulated by electric fields. In this manner, the risk of heart chamber fillibrations can be substantially reduced.

Frequently during high-frequency surgery other devices are operated, which require data transmission with high data transmission rates. Data are transmitted in digital or analog form between computers or other devices. These data can be measurement data or other values which are displayed on a screen. To this end, these data can be derived from any kind of image-transmitting systems, such as ultrasonic devices or X-ray devices. These data are processed further and recorded in computer systems or video processors. At certain times, falsification of these data can have especially critical results and substantially falsify the information content of these data. Therefore, an advantageous embodiment is if the measurement device for the determination of protected times determines, in particular, those time intervals in which these transmitted data are most interference prone. This is, e.g. the case if the data are transmitted for an off-line evaluation from a computer to the storage medium.

BRIEF DESCRIPTION OF THE DRAWINGS

The present invention is made more apparent in the following using preferred embodiments with reference to the accompanying drawing, to which is explicitly referred for the disclosure of all invented details not explained further herein, without the intention of limiting the scope or spirit of the overall inventive concept. Depicted is in.

DESCRIPTION OF A PREFERRED EMBODIMENT

Figure 1:
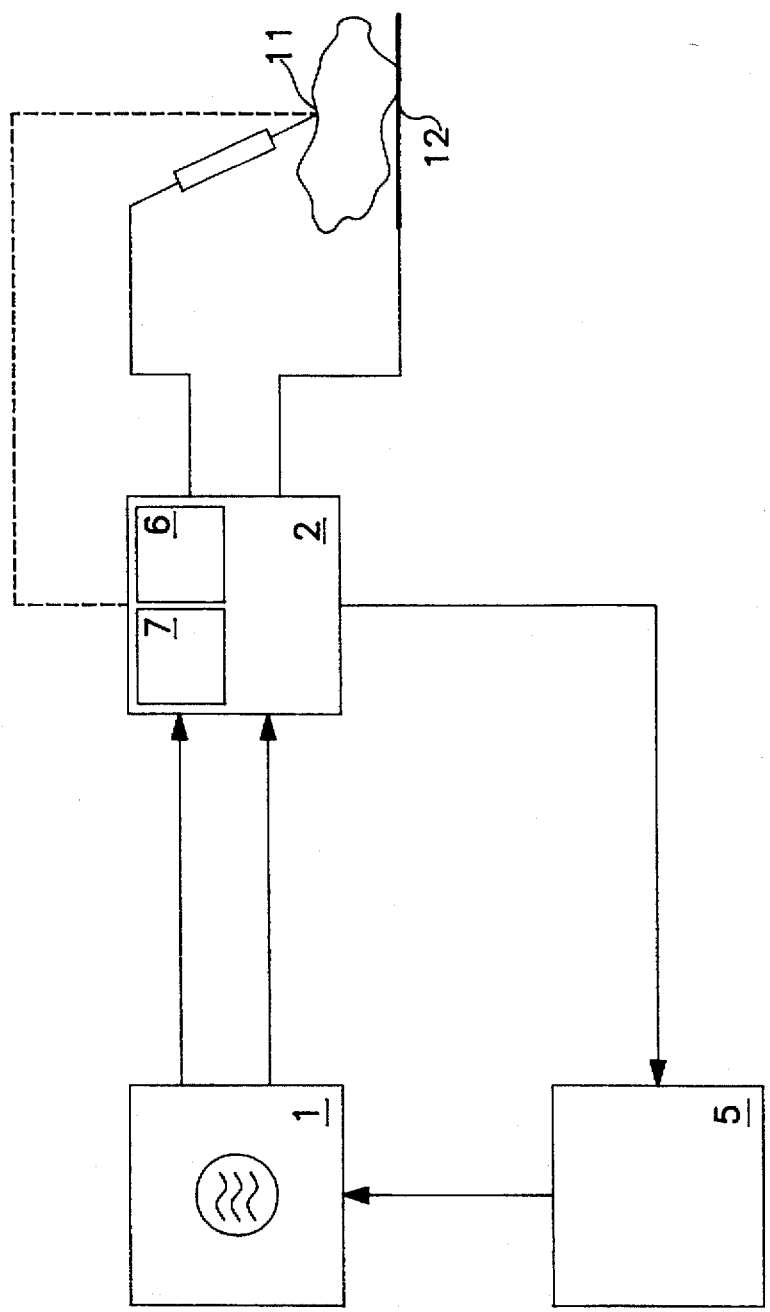
FIG. 1: A basic circuit diagram of the high-frequency surgical generator for cutting tissue.

FIG. 1 shows the basic circuit diagram of a high-frequency surgical generator with which undesired side effects during cutting tissue are largely reduced. The high-frequency generator 1 for high-frequency surgery is provided with adjustment devices for setting the momentary electric output values, such as e.g. current, voltage and power. The high-frequency current required for cutting is introduced into the tissue via a probe 11 and leaves the patient through the neutral electrode 12. The contacting surface of probe 11 is substantially smaller than the surface of the neutral electrode 12 so that the thermal effects, on which high-frequency surgery is based, occur at the probe 11. A measurement device 2 is provided for direct and/or indirect determination of cutting. This device may contain a measurement transmitter in the immediate vicinity of the probe. Moreover, it can contain an evaluation unit for evaluating the electric output values of the generator. The device for direct and/or indirect determination of cutting may selectively contain a test-signal generator 6, the test signal of which is transmitted to the probe and is measured with the aid of the measurement device 2. The measurement device may have a limit transmitter 7 which establishes the threshold for the condition "cutting".

Furthermore, the apparatus contains a desired-value transmitter 5 which provides the desired value for the output power or another electric value of the high-frequency generator proportional thereto corresponding to the output signal of the measurement device.

Figure 2A:
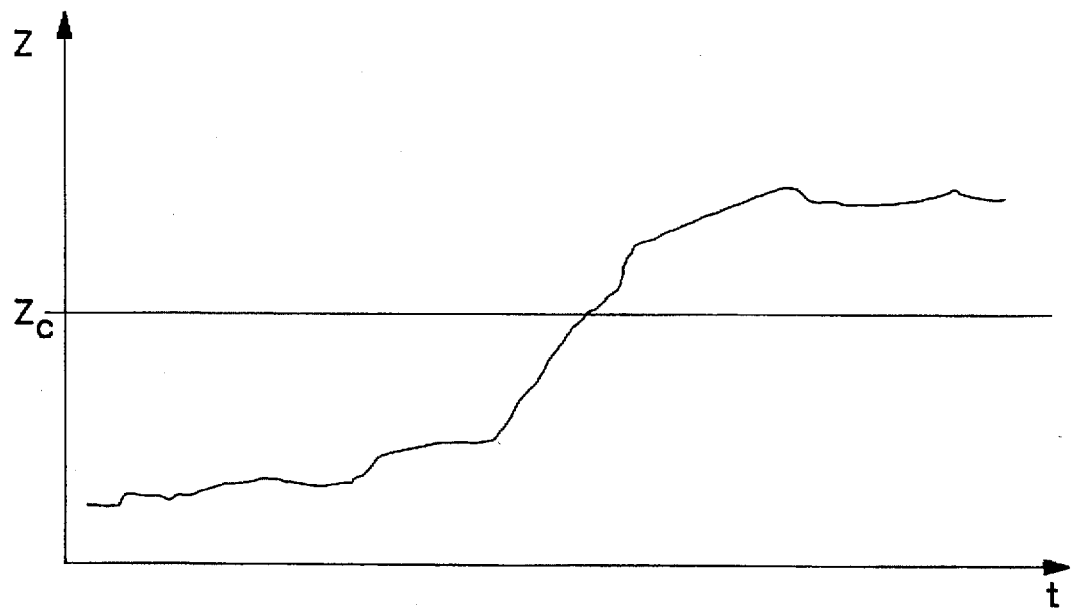
FIGS. 2(a) and 2(b): Are an exemplary representation of the rise in impedance at the commencement of cutting.
Figure 2B:
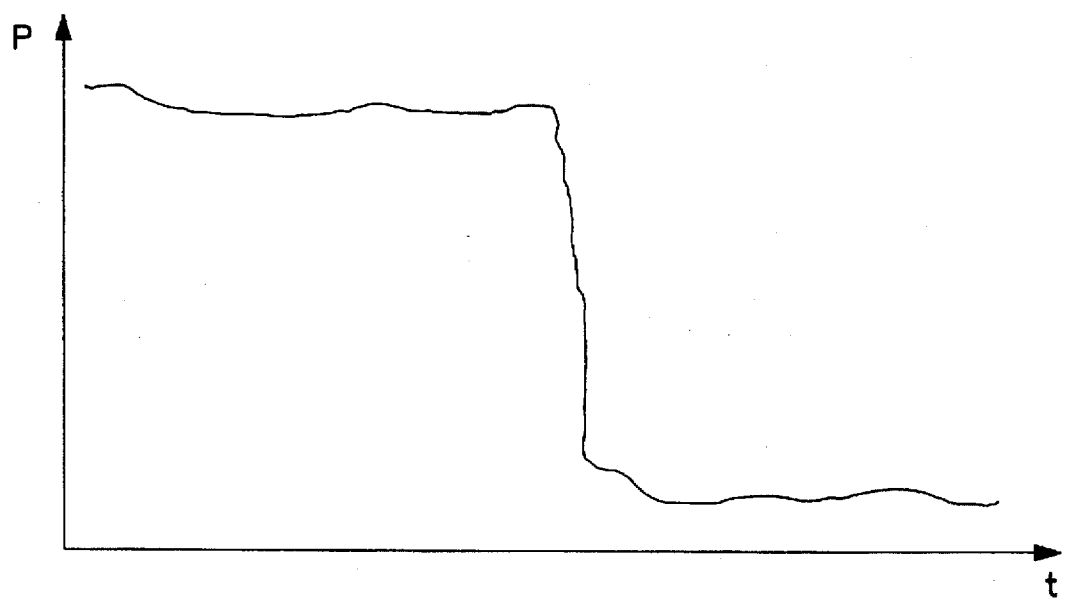

FIG. 2 shows the course of the tissue impedance at the commencement of a typical incision into the wall of the stomach or intestines, as was determined by numerous measurements. At first the tissue impedance is very low due to the conductive fluid on the surface. After sufficient energy has been delivered in order to vaporize this layer of fluid, the impedance rises sharply. It is not until then that an incision can be made. In order that only a minor delay occurs prior to the initial incision, it is necessary that the energy required for vaporizing the fluid is delivered as quickly as possible. The generator output power should, therefore, be as high as possible at the start of an incision. After commencement of cutting has been determined, e.g., by evaluation of the tissue impedance and comparison to a threshold value $Z_G$, the generator power may be lowered to a value usually sufficient for cutting.

Figure 3:
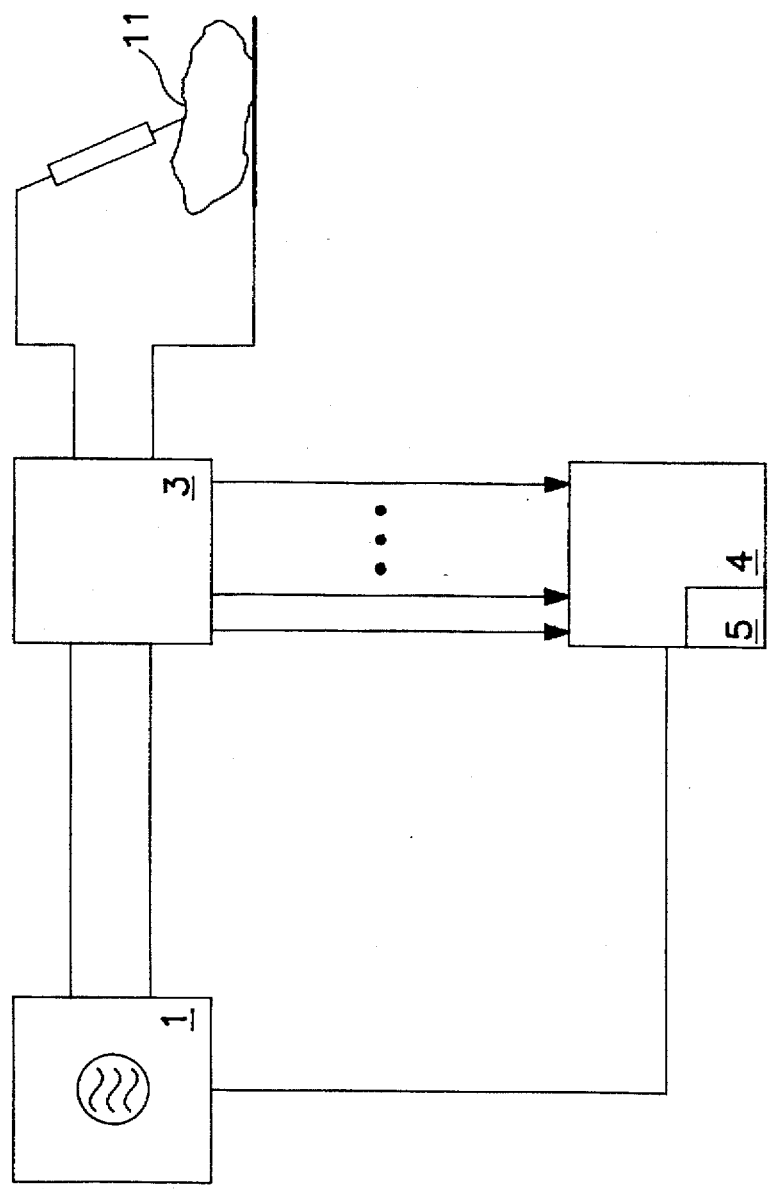
FIG. 3: A basic circuit diagram of the high-frequency surgical generator for performing tissue-dependent, respectively material-dependent surgery.

FIG. 3 shows the basic circuit diagram of a high-frequency surgical generator in which the power can be lowered to a safe value, by way of illustration upon contact with metal. The high-frequency generator 1 has a device for direct and/or indirect setting of the maximum output power. Between the high-frequency surgical generator 1 and the cutting electrode 11 is an indicator device 3 for indicating the power or a value dependent thereon with electric signals in two or several different frequency ranges. The electric output signals of this indicator device 3 are transmitted to an evaluation circuit 4. This evaluation circuit contains a desired-value transmitter 5 which provides the desired values for setting the high-frequency generator 1. The desired-value transmission occurs in dependence on the ratio of the output signals of the indicator device.

Figure 4:
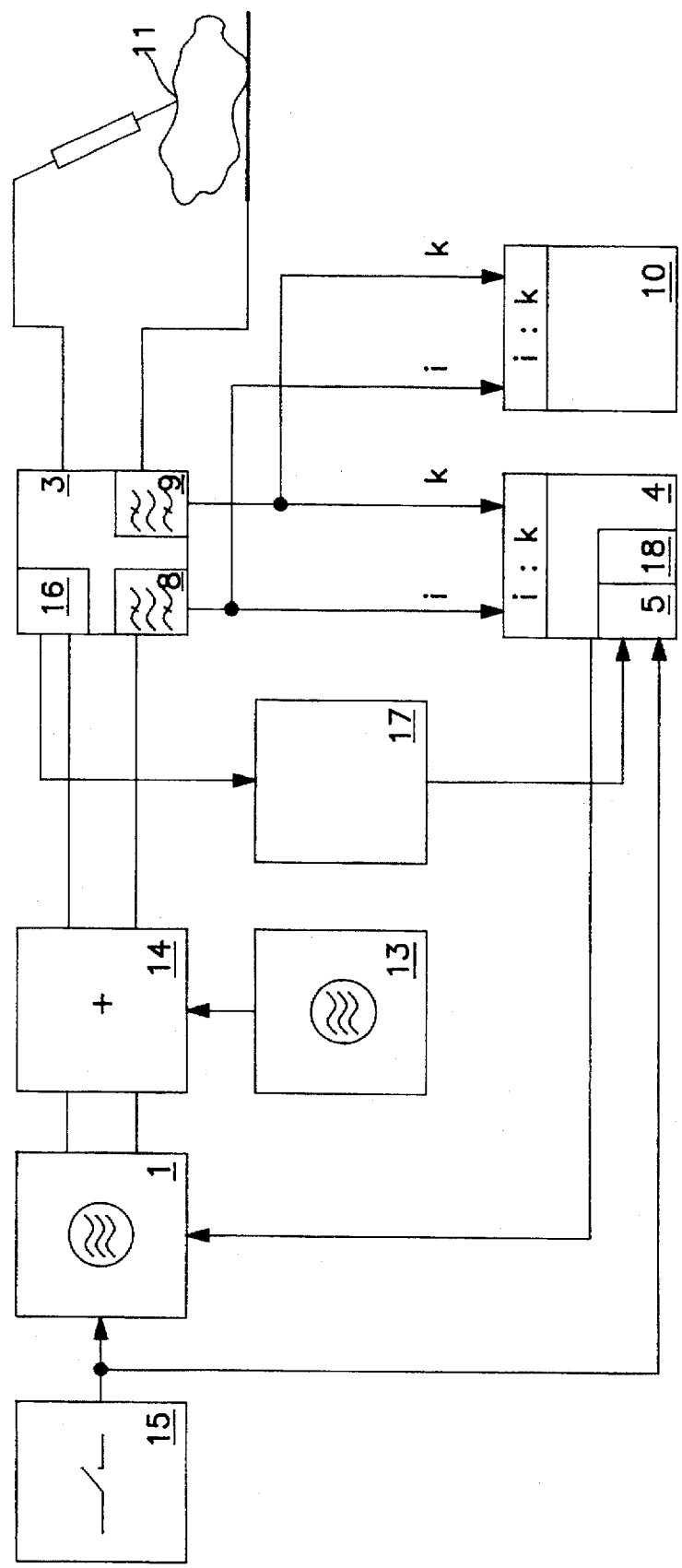
FIG. 4: A basic circuit diagram of the high-frequency surgical generator having supplementary devices for advantageous embodiments.

The intention of FIG. 4 is to show several advantageous embodiments. It contains all the elements of FIG. 1, which are described in the preceding section. The indicator device 3 has two filters 8 and 9 for selecting two different frequency ranges. The two electric output signals (i), (k) of the indicator device 3 may be selectively transmitted to a warning device 10 to warn the surgeon. This warning device is actuated if the ratio of the two output signals of the indicator device 3 exceeds a certain value. Furthermore, an additional auxilliary oscillator 13 is shown whose signal of low power is additively superimposed via the coupling element 14 to the output signal of the high-frequency generator. Switch 15 serves to activate the high-frequency generator. Moreover, it terminates the time interval for switching off the generator, generated by the timer in the evaluation circuit 4. Furthermore in the indicator device 3 there is a device 16 for determining the impedance of the tissue at the cutting electrode 11. This impedance is evaluated in an impedance evaluation circuit 17 and also utilized for terminating the time interval for switching off the generator.

Figure 5A:
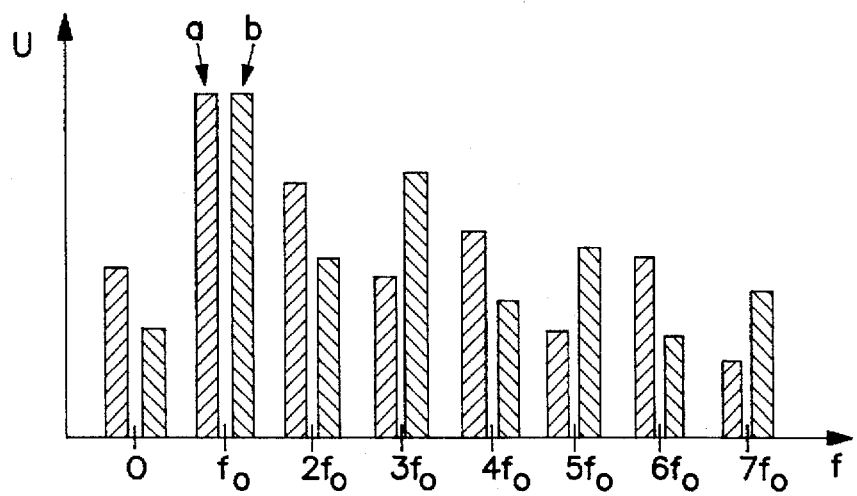
FIGS. 5(a), 5(b) and 5(c): Are an exemplary representation of the spectral distribution of the generator power and exemplary filter curves.
Figure 5B:
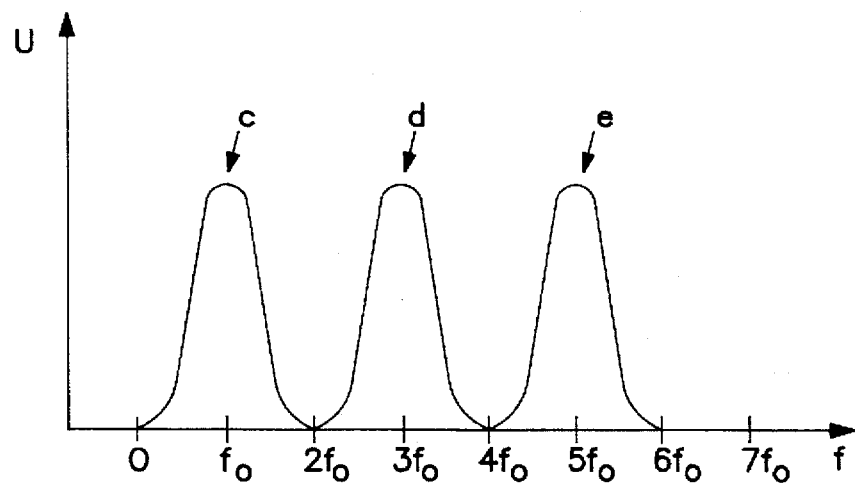
Figure 5C:
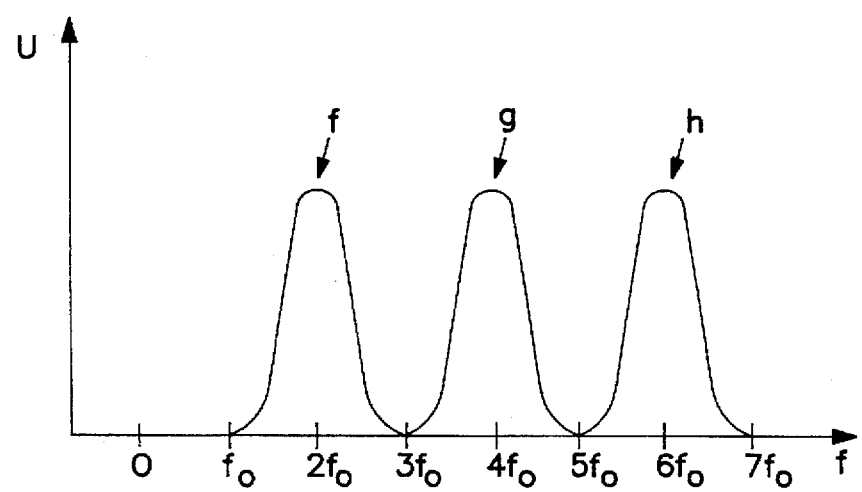

FIG. 5 shows, by way of example, the spectral lines of two different spectra, like they occur in a narrowband high-frequency generator. The voltage U is drawn as a representative value for one of the output values of the generator. The pairs of columns in the chart show the amplitudes at the multiples of the output values of the generator frequency $f_O$. The left column (a) of every pair shows the spectrum if there are great differences in the physical properties between the electrode material and the material to be cut. If both materials have similar physical properties, a spectrum may be yielded as shown by the right columns (b). Both spectra are normed to the same amplitude of the basic wave ($f_O$). The middle graph in FIG. 5 shows, by way of example, a possible spectral amplitude characteristic like the second filter 9 might have. For the evaluation, the selection of one of three frequency ranges (c), (d) or (e) illustrated, by way of example, suffices. Several such frequency ranges may also be combined. The bottom graph in FIG. 5 shows, by way of example, a possible amplitude characteristic like the first filter 8 should have. For the evaluation, the selection of one of the three frequency ranges (f), (g) or (h) illustrated, by way of example, suffices. In this case, too, several frequencies may be combined.

Figure 6:
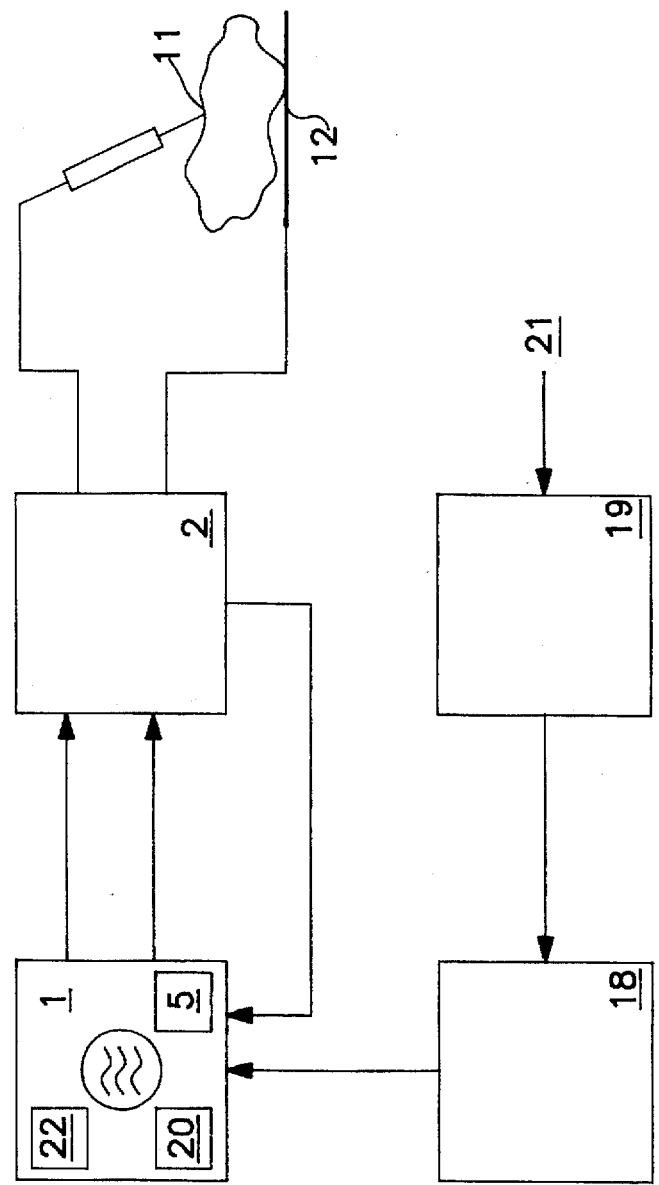
FIG. 6: A basic circuit diagram of the high-frequency surgical generator having minimal negative reactions on the surrounding area.

FIG. 6 shows the basic circuit of the invented high-frequency surgical generator. The output power of the high-frequency generator 1 for high-frequency surgery can be controlled. The high-frequency current is transmitted into the patient via the probe 11. The reflux of the high-frequency current occurs via the neutral electrode 12. A blanking-out device 18 regulates the generator 1 in such a manner that the output power is reduced in specific time intervals. These time intervals are provided by a device 19 for fixing the times to be protected from the generator power. To this device 19 is transmitted a signal 21 which reflects the patient's heart rhythm or other biological signals. To device 19 a signal can also be transmitted that comes from data processing systems and gives times in which an interference is particularly detrimental to functioning of the system. The device 22 fixes the internal conditions of the generator after the time intervals in which the generator is reduced. A desired-value transmitter 5 in the generator provides desired values for setting the generator. A measurement device 2 for determination of cutting detects the commencement of cutting and thereby controls the desired-value transmitter 5. A memory unit 20 in the generator permits storing the last internal conditions in the generator in order to ensure continuation of cutting with the same parameters.

Figure 7:
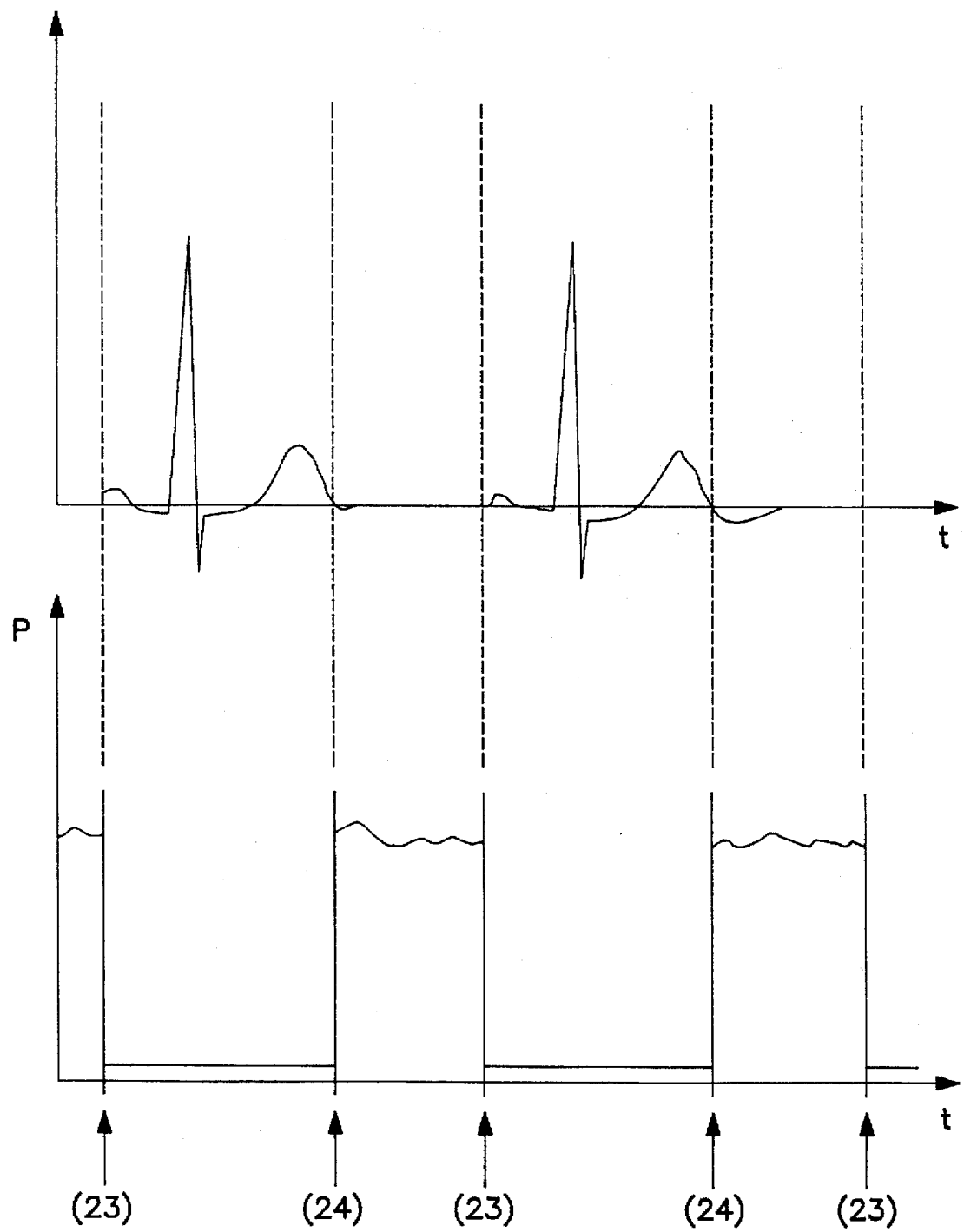
FIGS. 7(a) and 7(b): Are an exemplary representation of the synchronization to an electrocardiogram signal.

FIG. 7 shows, by way of example, the blanking-out device 18 controlled by an electrocardiogram signal. In the top diagram, the electrocardiogram signal is shown over the time. In the bottom diagram the temporal course of the generator power is shown schematically with the same time measure. The generator is activated here only at those times When a stimulation of the heart muscle or a pacemaker is not possible. Switching off the generator occurs at the points in time 23 at which storage in the memory unit is triggered. Activation of the generator and requesting the memory conditions occurs at the points in time 24.

What is claimed is:

1. A high frequency surgical generating system having a device for setting the maximum power output sufficient for tissue being operated on with respect to material detected at an operation site comprising:

a high frequency generator having an output; indicating means, said indicating means comparing a spectrum of power from said high frequency generator output influenced by electrical values dependent thereon; said indicating means comparing the power spectrum of at least two different frequency ranges; display means receiving and displaying an electric signal representing said power; an evaluating circuit receiving an output from said indicating means, said evaluating circuit having a desire-value transmitter for setting a desired output value from said high frequency generator that is dependent upon a ratio of a plurality of output signals representing said at least two different frequency ranges from said indicating means.

2. The system according to claim 1 in which said indicating means includes a pair of filters for evaluating spectral performance of said high frequency generating means; a first filter of said pair of filters detecting spectral performance of even harmonics of the basic frequency of said high frequency generator; a second filter of said pair of filters detecting spectral performance of odd harmonics of the basic frequency output of said high frequency generator;

said evaluating circuit having a regulated output regulated by said desired-value transmitter to reduce power output of said high frequency generator; and warning means providing a warning when a ratio of odd harmonics to even harmonics exceeds a preset value.

3. The system according to claim 2 including a low power auxiliary oscillator having an oscillation frequency of $f_H$; coupling means coupling said auxiliary oscillator to an output of said high frequency generator, said auxiliary oscillator signal being additively superimposed on the output signal of said high frequency generator; said first filter detecting even order distortions and said second filter detecting odd order distortions.

4. The system according to claim 3 in which one of said pair of filters is a lower pass filter having a bandpass extending substantially to 0 Hz.

5. The system according to claim 1 including timing means coupled to said desired value transmitting means, said timing means reducing and maintaining power output from said high frequency generator for a predetermined time interval, said time interval being between a minimum time interval corresponding to the duration of a half-wave of a high frequency signal from said high frequency generator and a maximum time interval corresponding to an off condition for activating said high frequency generator.

6. The system according to claim 5 including impedance detecting means in said indicating means; and an impedance evaluation circuit means for evaluating the detected impedance, said impedance evaluation circuit means terminating said reduced power output time interval when the detected impedance exceeds a preset impedance value.

* * * * *